United States Patent [19]

Knoff

[11] Patent Number: 4,909,084

[45] Date of Patent: Mar. 20, 1990

[54] FILAMENT SPECIMEN FIXTURE

[75] Inventor: Warren F. Knoff, Richmond, Va.

[73] Assignee: E. I. Du Pont de Nemours and Company, Wilmington, Del.

[21] Appl. No.: 305,443

[22] Filed: Feb. 2, 1989

[51] Int. Cl.<sup>4</sup> ............................................. G01N 1/00
[52] U.S. Cl. ........................................ 73/856; 73/830
[58] Field of Search ...................... 73/863, 864.41, 856, 73/857, 858, 859, 860, 828, 830

[56] References Cited

U.S. PATENT DOCUMENTS 3,855,850  12/1974  Norskog ............................ 73/856 X
3,885,424  5/1975  Ryckman et al. ...................... 73/860

Primary Examiner—Jerry W. Myracle

[57] ABSTRACT

A single-filament specimen preparation fixture for preparing a multiplicity of tensile testing specimens from the same filament. The fixture can be used manually or it can be adapted for use as one element in an automatic testing system.

5 Claims, 2 Drawing Sheets

FILAMENT SPECIMEN FIXTURE

BACKGROUND OF THE INVENTION

1. Field of the Invention

This invention relates to a fixture for preparation of single-filament specimens for tensile testing. The fixture can be used in automated testing procedures or it can be used for the preparation of specimens to be tested manually.

2. Description of the Prior Art

Tensile testing of materials is time consuming and proper preparation of specimens for such testing is tedious and difficult. Recently, automated tensile testing systems have been developed wherein robots are designed to conduct tensile testing automatically using specimens which have been previously prepared and loaded into the testing machine. Such a system is well adapted for testing materials which use the traditional "dog bone" form of specimens. An automated system is described by R. L. Scott and J. K. Rieke in Advances in Laboratory Automation Robotics 1984 (Boston): pp 151–164 (Sept. 16–18, 1984; c1984 Zymark Corporation, Hopkinton, MA 10748).

Preparation of specimens is especially tedious and difficult in testing fibers and even more so when the tests are to be conducted on single filaments which may be less than one denier in linear density (that is, on the order of 0.0005 inch in diameter). Until the present invention, filament tensile specimens have been made on a one-at-a-time basis with no opportunity to make several specimens from a single length of one filament. ASTM D 3379-75 (Reapproved 1982) describes the generally-used preparation of single filament tensile testing specimens.

SUMMARY OF THE INVENTION

The present invention provides a single-filament sampling preparation fixture comprising a platen with two spaced-apart filament aligning means, two filament clamping means on a straight line with the filament aligning means and located with one clamping means adjacent to each aligning means, cutting grooves in the platen, between the aligning means, and intersecting the straight line, a centering hole in the platen, with the center of the hole about midway between the cutting grooves and on the straight line.

The platen can, also, have a filament mounting tab relief cut in the top surface to receive individual filament mounting tabs between the cutting grooves. There can be a multiplicity of cutting grooves and centering holes on the platen.

DETAILED DESCRIPTION OF THE INVENTION

The filament specimen fixture of this invention can be used to prepare tensile testing specimens for use with an automated system or for use manually. The fixture can be made to conform to the needs of an automated system with manual placement only of the mounting tabs and the filament itself. After placement of the mounting tabs and the filament to be tested, a robot can be set automatically to adhere the filament to the mounting tabs, cut the filament between the tabs, and place the thus-prepared specimens in a tensile testing machine to be pulled.

The fixture of this invention permits preparation of single filament specimens rapidly and conveniently. The fixture of this invention permits a great savings in time and provides a specimen preparing means which assures specimens of consistently high quality.

This fixture provides a means by which multiple tensile testing specimens can be prepared from the same single filament. This sampling procedure allows estimates of the variability in tensile properties along a single filament. Such information is not available if single specimens are prepared from several separate filaments. The fixture of this invention would make much simpler and more accurate the specimen preparation for study such as that disclosed in Journal of Materials Science, vol. 22, (1987) pp 1024–1030.

In general operation, single-filament specimens are prepared for tensile testing using the fixture of this invention and the specimens are then pulled on a standard tensile testing apparatus. The samples for tensile testing are filaments mounted by means of an adhesive onto a mounting tab. The tab and the filament are then mounted into the jaws of the tensile testing apparatus and the mounting tab is cut to leave the filament as the only connection between the tensile tester jaws.

Figure 1:
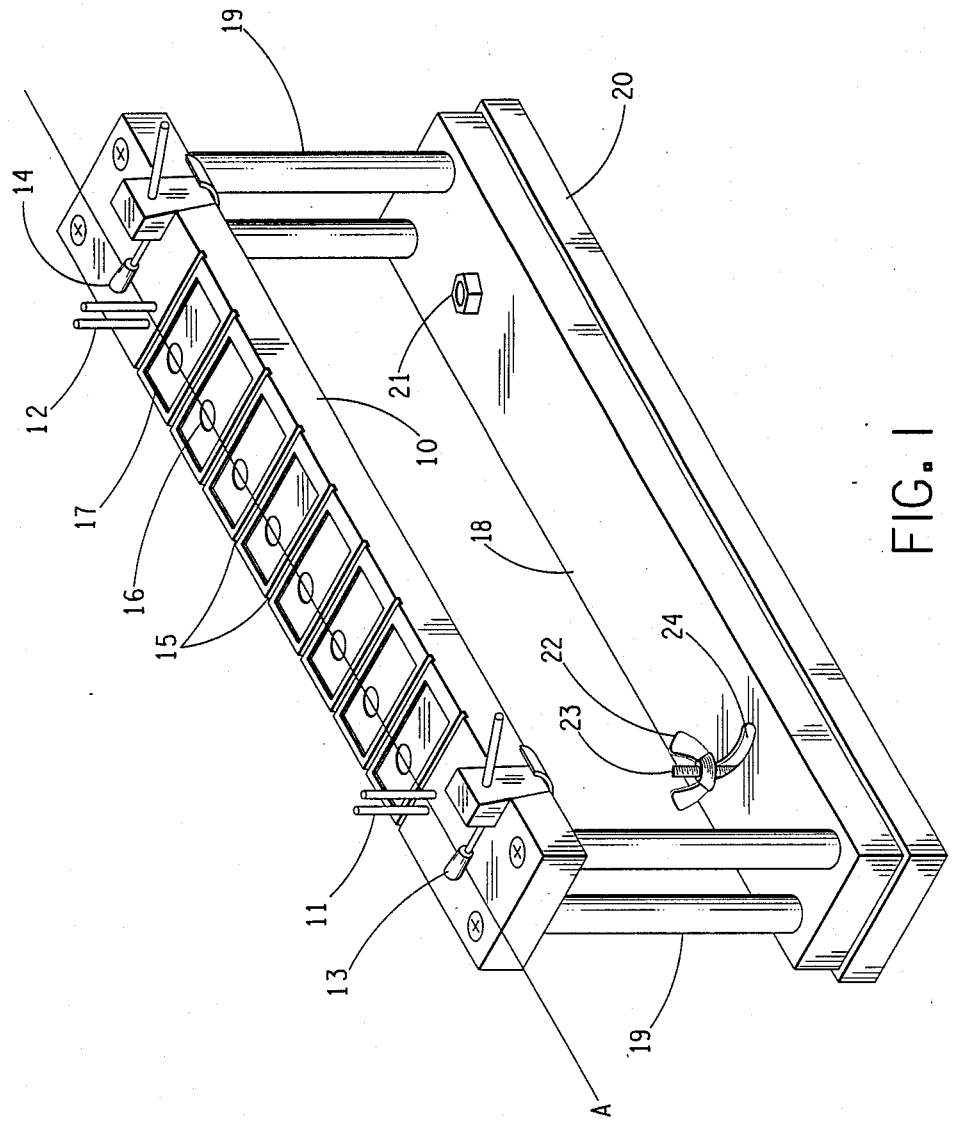
FIG. 1 is a perspective drawing of the fixture of this invention.

In FIG. 1, the filament sampling preparation fixture of this invention includes platen 10 with filament aligning means 11 and 12 spaced apart on the platen and filament clamping means 13 and 14 on the platen adjacent to the filament aligning means. Platen 10 has cutting grooves 15 and centering holes 16, all located in a straight line between aligning means 11 and 12. Cutting grooves 15 are spaced regularly along and intersecting that straight line between the aligning means. As a general rule, the cutting grooves 15 are made parallel with each other and perpendicular to that straight line; but such is not necessary. The grooves could be at an angle to the straight line; and, if desired or required for some purpose, could be nonparallel. Centering holes 16 are cut in platen 10 with the center of the holes about midway between cutting grooves 15 and on the straight line between filament aligning means 11 and 12. The fixture of this invention can have as many cutting grooves 15 and associated centering holes 16 as are desired or convenient for any given application.

As will be discussed below, the specimen preparation for which the fixture of this invention is used requires the aligned presence of a filament mounting tab. The filament mounting tab is slightly smaller than the area bounded by the edges of platen 10 and adjacent cutting grooves 15. To enable positive placement of the filament mounting tabs, a relief 17 can be cut into the surface of the platen having a size slightly larger than that of the mounting tabs.

In one embodiment, platen 10 is affixed to a platen support 18 by means of standards 19. Platen support 18 is adapted to provide adjustment for location of the platen by being attached to base 20, such as by using bolt 21 for a pivot at one end of platen support 18 and wing nut 22 with bolt 23 through arcuate hole 24 for platen aligning means in the other end of platen support 18.

Figure 2:
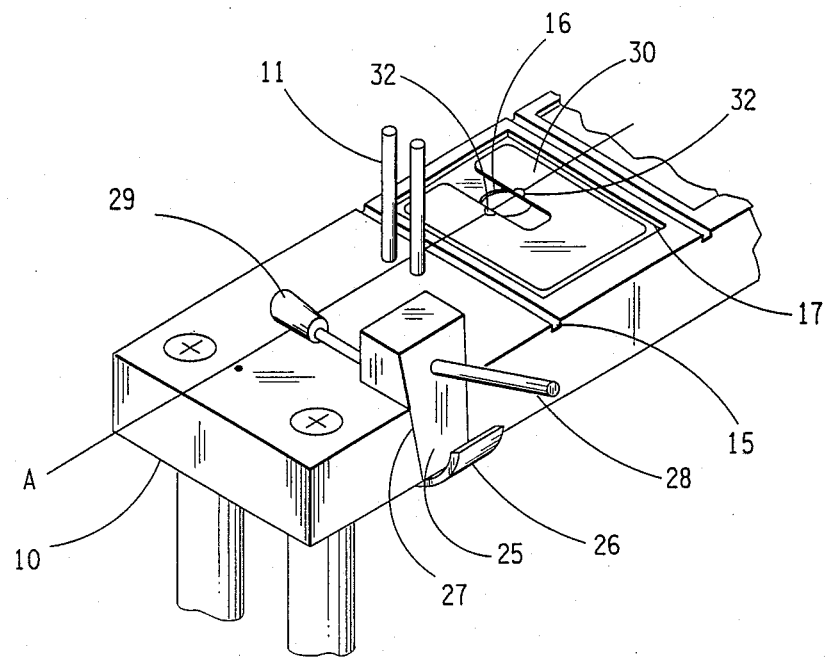
FIG. 2 is a close-up perspective drawing of a portion of the fixture of this invention.

FIG. 2 depicts a portion of the fixture of this invention at a larger scale than is presented in FIG. 1. Platen 10 is shown with filament aligning means 11 and filament clamping means 13. Filament clamping means 13 includes a support 25 held by spring 26 to be pivotable in slot 27 in platen 10. Shaft 28 extends through support 25 and includes pressure pad 29 which is biased against platen 10 in the straight line from filament aligning means 11 and 12. FIG. 2 also depicts cutting groves 15 and centering holes 16 in a larger scale, and includes a representation of a mounting tab 30 in place in relief 17.

In use, mounting tabs 30 (having two arms 31 and a throat 33, see FIG. 3) are placed on the platen and a filament A is placed on platen 10, over mounting tabs 30, and between filament aligning pins 11 and 12. Filament clamping bars 13 and 14 are moved into position against platen 10 to hold filament A against the platen. The filament, thus, passes over cutting grooves 15 and centering holes 16. Beads of adhesive 32 are placed over filament A at the inside edges of each mounting tab arm 31 and, when the adhesive has hardened, the filament A is cut at each cutting groove 15. A filament sample is, thus, completed and ready for use in the conduct of a tensile test.

Figure 3:
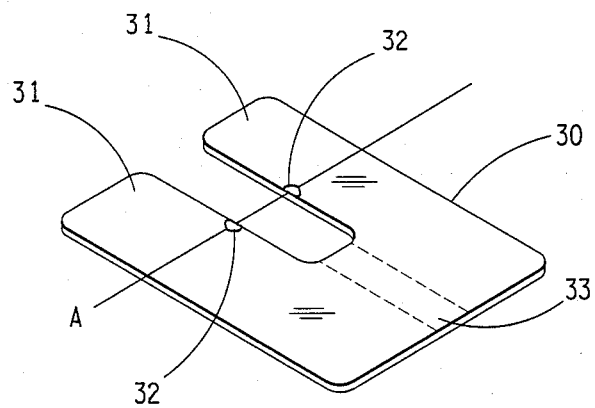
FIG. 3 is a drawing of a filament mounting tab and filament prepared in the fixture of this invention.

To conduct a tensile test of the filament A, a mounted sample, as shown in FIG. 3, is placed between the jaws of a tensile testing machine and, when the jaws have been closed, the throat 33 of the mounting tab is clipped away, leaving only filament A between the machine jaws. The filament A is pulled to break and results in terms of stress and strain are evaluated using the distance between inside edges of mounting tab arms 31 as the gage length.

I claim:

1. A filament specimen preparation fixture comprising:
   a platen with
   (i) two spaced-apart filament aligning means,
   (ii) two filament clamping means on a straight line with the filament aligning means and located with one clamping means adjacent to each aligning means,
   (iii) cutting grooves in the platen, between the aligning means, and intersecting the straight line,
   (iv) a centering hole in the platen, with the center of the hole about midway between the cutting grooves and on the straight line.

2. The fixture of claim 1 wherein there are a multiplicity of centering holes with cutting grooves adjacent to both sides of each centering hole.

3. The fixture of claim 1 wherein the clamping means are spring biased to the platen.

4. The fixture of claim 1 wherein the cutting grooves are parallel.

5. The fixture of claim 4 wherein the cutting grooves are perpendicular to the straight line.

* * * * *